(12) United States Patent
Urs

(10) Patent No.: US 8,321,184 B1
(45) Date of Patent: Nov. 27, 2012

(54) METHOD FOR CHARACTERIZING LENSES

(75) Inventor: Raksha Urs, Miami, FL (US)

(73) Assignee: Vision CRC Limited, Sydney (AU)

( * ) Notice: Subject to any disclaimer, the term of this patent is extended or adjusted under 35 U.S.C. 154(b) by 699 days.

(21) Appl. No.: 12/380,201

(22) Filed: Feb. 25, 2009

Related U.S. Application Data

(60) Provisional application No. 61/031,023, filed on Feb. 25, 2008.

(51) Int. Cl.
*G06F 7/60* (2006.01)
*G06F 17/10* (2006.01)

(52) U.S. Cl. .......................................................... 703/2

(58) Field of Classification Search .................. 703/2, 1
See application file for complete search history.

(56) References Cited

U.S. PATENT DOCUMENTS

| | | | |
|---|---|---|---|
| 7,740,520 B2 * | 6/2010 | Hatano et al. ...................... | 451/5 |
| 2006/0274262 A1 * | 12/2006 | Andino et al. ................. | 351/159 |

OTHER PUBLICATIONS

Kasprzak, Henry, "New Approximation for the Whole Profile of the Human Crystalline Lens", Ophthal. Physiol. Opt. 2000, pp. 31-43, vol. 20, No. 1.*
Koretz et al., "Analysis of Human Crystalline Lens Curvature as a Function of Accommodative State and Age", Vision Res., 1984, pp. 1141-1151, vol. 24, No. 10.*
Einighammer, Jens, "The Individual Virtual Eye", Feb. 13, 2008, pp. (xi, 26, 29, 113).*
Stewart "Calculus 3rd Edition". 1995 Brooks/Cole Pubslishing Company. 7 Pages.*
Abolmaali et al., "Sensitivity Study of Human Crystalline Lens Accommodation", Computer Methods and Programs in Biomedicine, 2007, pp. 77-90, vol. 85.
Augusteyn et al., "Biometry of Primate Lenses During Immersion in Preservation Media", Molecular Vision, 2006, pp. 740-747, vol. 12.
Brown, Nicholas, "The Change in Shape and Internal Form of the Lens of the Eye on Accommodation", Exp. Eye Res., 1973, pp. 441-459, vol. 15.
Burd et al., "Numerical Modelling of the Accommodating Lens", Vision Research, 2002, pp. 2235-2251, vol. 42.
Burd et al., "Rapid Communication Mechanics of Accommodation of the Human Eye", Vision Research, 1999, pp. 1591-1595, vol. 39.
Denham et al., "Shadow Photogrammetric Apparatus for the Quantitative Evaluation of Corneal Buttons", Ophthalmic Surgery, 1989, pp. 794-799, vol. 20, No. 11.
Dubbelman et al., "Change in Shapre of the Aging Human Crystalline Lens with Accommodation", Vision Research, 2005, pp. 117-132, vol. 45.
Dubbelman et al., "The Shape of the Aging Human Lens: Curvature, Equivalent Refractive Index and the Lens Paradox", Vision Research, 2001, pp. 1867-1877, vol. 41.
Hermans et al., "Change in the Accommodative Force on the Lens of the Human Eye with Age", Vision Research, 2008, pp. 119-126, vol. 48. Hermans et al., "Estimating the External Force Acting on the Human Eye Lens during Accommodation by Finite Element Modelling", Vision Research, 2006, pp. 3642-3650, vol. 46.
Howcroft et al., "Aspheric Curvatures for the Human Lens", Vision Res., 1977, pp. 1217-1223, vol. 17.

* cited by examiner

*Primary Examiner* — Eunhee Kim
(74) *Attorney, Agent, or Firm* — Smith Moore Leatherwood LLP

(57) ABSTRACT

Methods for describing the shape of a lens are disclosed comprising mathematically dividing said shape into substantially two halves and providing at least one mathematical function comprising mathematically linear combinations of polynomials, wherein at least one half is described by said mathematical function, and wherein said method is applicable to a surface of at least one half selected from the group consisting of rotationally symmetric surfaces and non-rotationally symmetric surfaces.

2 Claims, 14 Drawing Sheets
(14 of 14 Drawing Sheet(s) Filed in Color)

METHOD FOR CHARACTERIZING LENSES

CROSS REFERENCE

This application claims benefit of priority from U.S. Provisional Patent Application Ser. No. 61/031,023, filed Feb. 25, 2008, which is incorporated by reference herein as if made part of the present specification.

FIELD OF THE INVENTION

Embodiments of the present invention relate generally to the field of lens design and lens characterization. More specifically, embodiments of the present invention relate to methods and apparatuses for developing age dependent mathematical models of the isolated ex-vivo human crystalline lens shape for use in modeling and design of crystalline lens prosthetics.

BACKGROUND

Presbyopia and cataract are two of the most common disorder to beset human vision, especially for the aged. Presbyopia is the loss of the ability of the eye to change focus for near vision. This change is associated with a loss in the ability of the crystalline lens of the eye to change shape. The onset of presbyopia is typically around 40 to 50 years of age. When presbyopia manifests in a person, they will no longer have the ability to attain clear vision for reading or seeing objects up close. This is currently most commonly corrected by the prescribing of reading glasses, bifocal, multifocal or aspheric progressive spectacles and contact lenses. Cataract is a disorder of the eye characterized by a loss of optical clarity of the crystalline lens. The individual with cataract will gradually lose vision in the affected eye. The current method for treating cataract is by removal of the crystalline lens (or its contents) and replacement of the lens with an intraocular lens (IOL) to restore correct distance focus. However, with conventional IOL implantation following cataract surgery, near vision is loss.

To overcome the problem of loss of near vision in presbyopia and post-cataract surgery, and to restore true accommodation (the ability of the eye to change continuous focus) some technologies have become available recently including accommodating IOL (AIOL) such as Crystalens, or Human-optic 1CU. Many others are currently in design and development stages. These include two-element AIOL (e.g. Synchrony by Visiogen) and other AIOLs (e.g. Nulens). A more natural strategy for restoring accommodation in the presbyope would involve, not the use of optical/mechanical devices such as those mentioned above, but the refilling of the crystalline lens with a soft material. This is a preferred option as the origin of presbyopia stems from a loss of softness of the content of the crystalline lens. Hence, a lens content replacement approach would be the most direct method for restoring accommodation. There are a number of ways by which this could be accomplished. The most direct method (sometimes called "phaco ersatz"; after Parel) involve the injection of a soft gel into the capsule of the crystalline lens to replace the (removed) hardened lens content of the presbyopic eye. Another method (after Nishi) involves the implantation of a bag-like device into the capsule and then fill the bag-like device with a soft gel. Finally, a pre-formed and pre-shaped lens (after Fine) which can be thermally distorted to facilitate introduction into the lens capsule, and its original shape re-established by thermal 'plastic memory' may be used.

For all of these methods mentioned above (which we hereafter call "crystalline lens prosthetics" methods), an optimum visual outcome can only be achieved if good knowledge of the shape of the natural crystalline lens as well as the most preferred optimum shape of the refilled lens is available.

It is an objective of the present invention to provide a method by which the surface shape (both anterior and posterior) of the natural crystalline lens and the shape of a crystalline lens prosthetic can be measured, described and used for the design and manufacture of optimum crystalline lens prosthetics.

Numerous analytical and finite element (FE) mechanical models of the human crystalline lens have been developed to simulate changes in lens shape during accommodation. Analytical models have been used to describe the accommodative mechanism in the human eye (Koretz and Handelman 1982) and to investigate the effects of lens elastic anisotropy on accommodation (Koretz and Handelman 1983). FE models have been used to demonstrate that Helmholtzian mechanism of accommodation is most likely for the young lens (Burd, Judge and Flavell 1999), to show that the 29 year old lens is more effective in accommodating than the 45 year old lens (Burd, Judge and Cross 2002), to compare Coleman and Helmholtzian accommodation theories (Martin, Guthoff, Terwee and Schmitz 2005), to estimate the external force acting on the lens during accommodation (Hermans, Dubbelman, van der Heijde and Heethaar 2006) and to show that the maximum zonular tension decreases with age and is the most likely cause for the decrease in accommodative amplitude with age (Abolmaali, Schachar and Le 2007). More recently FE models have been used to analyze the relationship between lens stiffness and accommodative amplitude (Weeber, van der Hiejde 2007) and to determine the change in accommodative force with age (Hermans, Dubbelman, van der Heijde and Heethar 2007). FE models provide valuable information about accommodation and presbyopia. The quality of the models depends on the geometric information used to develop them. Therefore accurate geometric representation of the human crystalline lens is a critical issue for FE modeling, especially at the equatorial regions where the forces are applied.

Burd et al. (2002) and Martin et al. (2005) used geometric information recorded by Brown (1973) to develop models for lenses aged 11, 29 and 45 and therefore their studies are limited to these three ages. Hermans et al. (2006) developed their model using lens shape obtained from Scheimpflug imaging. The images contain only the central portion of the anterior and posterior surfaces of the lens. Missing regions were modeled using two conic functions. Abolmaali et al. (2007) developed their model using information from published MRI images. Their model was not age dependent. Weeber et al (2007) used geometrical information based on in-vivo measurements (Dubbelman, van der Heijde & Weeber 2005; Strenk, Semmlow, Strenk, Munoz, Gronlund-Jacob & DeMarco 1999).

We have found that FE models should account for age dependency of the lens shape and should be based on measurements of the lens shape when no stresses are applied. The isolated ex-vivo lens is not subjected to any active external forces and can therefore serve as the basis for a geometric model that can be used in finite element modeling (FEM) studies.

The human crystalline lens is composed of two aspherical surfaces, which have been modeled with a number of mathematical functions. The earliest eye model represents the lens as two spherical surfaces. The shape has been progressively described as hyperbolic (Howcraft and Parker 1977) parabolic (Koretz, Handelman and Brown 1984) fourth order polynomial (Strenk, Strenk, Semmlow and DeMarco 2004) and conic functions (Dubbelman, van der Hiejde 2001, Rosen, Denham, Fernandez, Borja, Ho, Manns, Parel & Augusteyn 2006). While these models present a good approximation of the human lens, they were developed for optical modeling and therefore mostly focus on the central 4 to 5 mm of the lens, but not for providing much information about the equatorial region. Kasprzak (2000) approximated the whole profile of the human lens using a hyperbolic cosine function. This model is based on published values of radius of curvature and asphericity and focuses on the central optical zone of the lens. While this model has been evaluated against hyperbolic, parabolic and elliptic approximations, it has not been compared to an actual lens shape and therefore, the validity of the equatorial regions of this model is not known. Furthermore this approximation is a relatively complex expression and may not be easy to implement in FE models.

SUMMARY OF THE INVENTION

According to embodiments of the present invention, an age dependent mathematical model of the isolated ex-vivo human crystalline lens shape has now been developed for use in finite element modeling. Profiles of whole isolated human lenses (n=22) aged 26 to 82, were measured from shadow-photographs and fit to tenth order polynomials. Two methods were used to analyze the lenses. The Two Curves Method (TCM) used separate equations for the anterior and posterior surfaces of the lens. The One Curve Method (OCM) assumed symmetry around the optical axis and fit half of the contour of the lens. The age dependence of the polynomial coefficients was assessed. The analysis was used to produce an age-dependent polynomial model of the whole lens shape. According to one embodiment of the present invention, the root mean squared errors for the fits ranged from 41 to 122 µm for the OCM, 8 to 30 µm for the posterior surface of the TCM and 11 to 41 µm for the anterior surface of the TCM. Coefficients of the first, fifth and ninth term of the anterior surface of the TCM decreased with age. Coefficients of the third and seventh terms of the anterior surface of the TCM and the eighth term of the OCM increased with age. The coefficients of all other terms did not show any significant trend with age. According to embodiments of the present invention, the age dependent equation of the OCM provides a reliable model from age 20 to 70, and the shape of the whole human crystalline lens can be accurately modeled with tenth order polynomial functions. The models, according to the present invention, can serve to improve FE-models of lenses and provide the basis by which measurement and quantitative description of a natural crystalline lens or a crystalline lens prosthetic can be facilitated, and a basis by which design of optimum crystalline lens prosthetics can be supported and manufactured.

Further objects, advantages and embodiments of the invention will become evident from the reading of the following detailed description of the invention wherein reference is made to the accompanying drawings.

DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Herein we propose two models of the whole isolated ex-vivo human crystalline lens as a function of age using tenth order polynomials. The models are based on measurements obtained from shadow photographs of 22 lenses ranging in age from 26 to 82.

EXAMPLES

Lens Preparation

All human eyes were obtained and used in compliance with the guidelines of the Declaration of Helsinki for research involving the use of human tissue. The 22 crystalline lenses used in this study were from whole, intact cadaver eyes, in the age range of 26 to 82, obtained from American Eye Banks. The postmortem time varied from 1 to 5 days, during which time the whole eyes (globes) were stored at 2-6° C. in sealed jars on a bed of gauze, moistened with saline. Ophthalmic surgeons removed the cornea and iris using an operating microscope. The lens was extracted by carefully cutting the zonules and adherent vitreous using Vannas scissors. Wire lens spoons (Segal Instruments, Bombay, India) were used to immediately place the lens on the sutures of the testing cell, which was pre-filled with a DMEM solution (Augusteyn, Rosen, Borja, Ziebarth, & Parel, 2006). The time from lens extraction to measurement was approximately 6 minutes. Lens capsule integrity was visually inspected using the optical comparator (Rosen et al. 2006). Torn capsules usually appeared as surface irregularities or small flaps of tissue protruding from the capsule surface. Images of 94 human crystalline lenses were available. Of these, 29 lenses were excluded due to a capsule tear or cataractous changes and 43 lenses were excluded because they exhibited capsular separation, leaving 22 lenses for this study.

Shadow Photogrammetry

Figure 1:
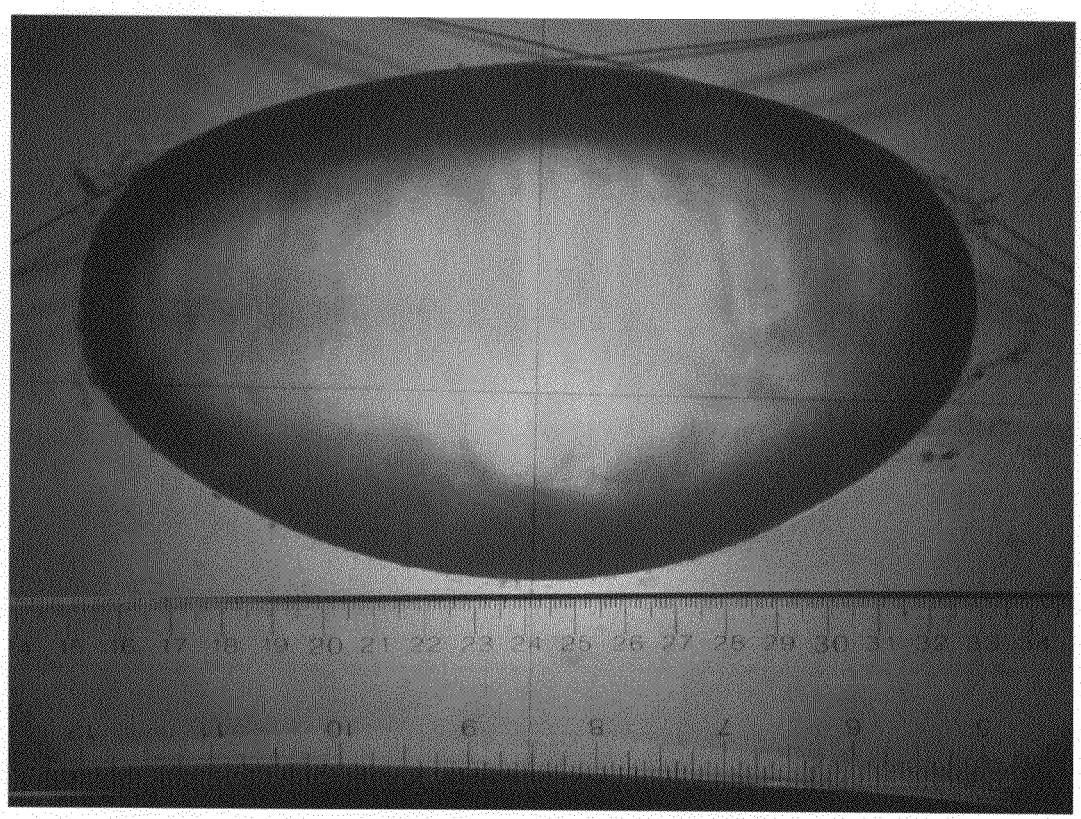
FIG. 1 is a shadow photograph of a human crystalline lens.

The technique of shadow photogrammetry of eye tissues has been described in detail in earlier publications (Denham, Holland, Mandelbaum, Pflugfelder & Parel, 1989; Pflugfelder, Roussel, Denham, Feuer, Mandelbaum & Parel, 1992; Rosen et al. 2006; Augusteyn et al, 2006). A modified optical comparator (BP-305, Topcon, Tokyo, Japan) projects a 20× magnified shadow of an excised lens onto a viewing screen. Two light sources, one for retroillumination and the other for sagittal illumination, enable photography of the lens in the coronal and sagittal views. The immersion cell described in Rosen et al. (2006) was modified by replacing the lens-holding ring with a supporting mesh made of 10-0 nylon sutures. This enabled the entire posterior surface of the lens to be available for contour detection (FIG. 1). A 4.0 Mp Nikon Coolpix 4500 digital camera (Tokyo, Japan) was used to capture the coronal and sagittal views of the lens. A ruler was also photographed on the same images for scaling purposes.

Image Analysis

The images were preprocessed with Canvas 9.0 (ACD Systems of America, Miami, Fla.). They were scaled against the ruler included in the image and were adjusted for magnification (20×) of the comparator. The images were then cropped to remove the ruler. The preprocessed images were loaded into Matlab (Mathworks, Inc., Natick Mass.) and converted to grayscale. An algorithm composed of two separate processes was used to detect the lens-contour. The first process detected a thick approximate contour of the lens, using the Prewitt edge detector and morphological functions. This eliminated false edges generated by the sutures and lens material. The second separate process used the Canny edge detector, to detect a fine contour of the lens. An intersection of the outputs of the two processes produces the lens contour with minimal false contours. A few false contours that were detected were removed manually. For the majority of the images, the size of each pixel in the plane of the lens was between 4 and 5 μm.

Figure 2:
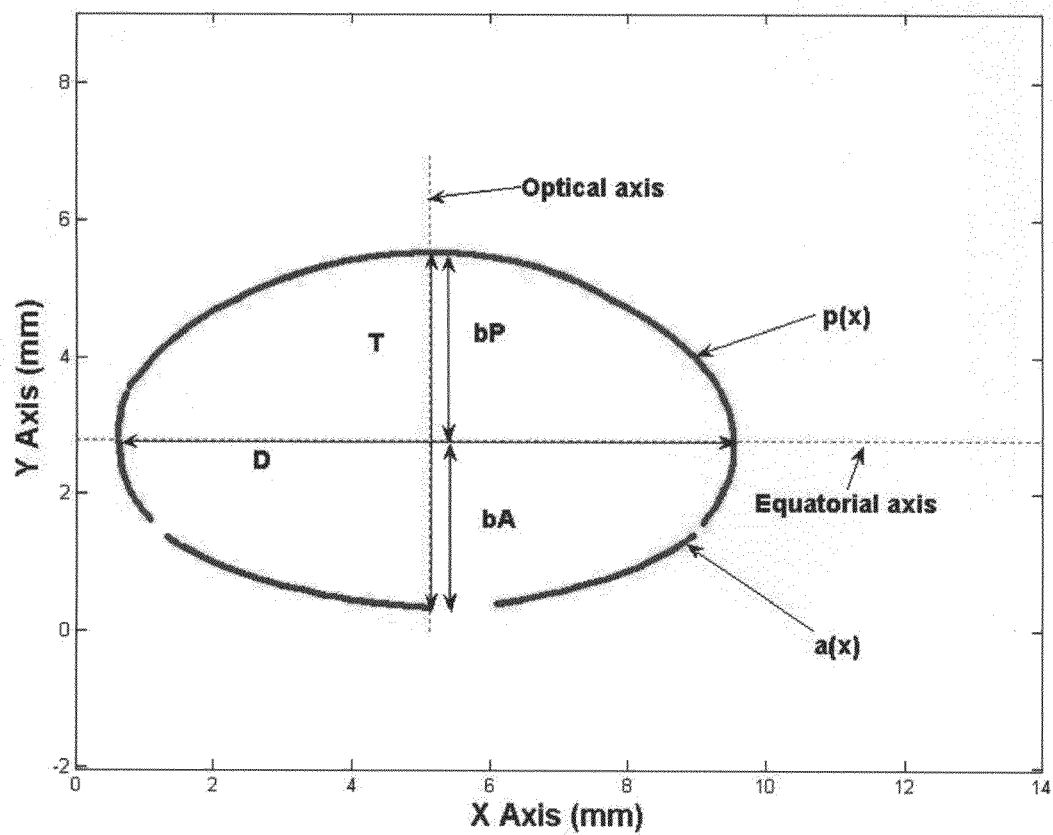
FIG. 2 is a plotted coordinate system showing the Two Curves method.
Figure 3:
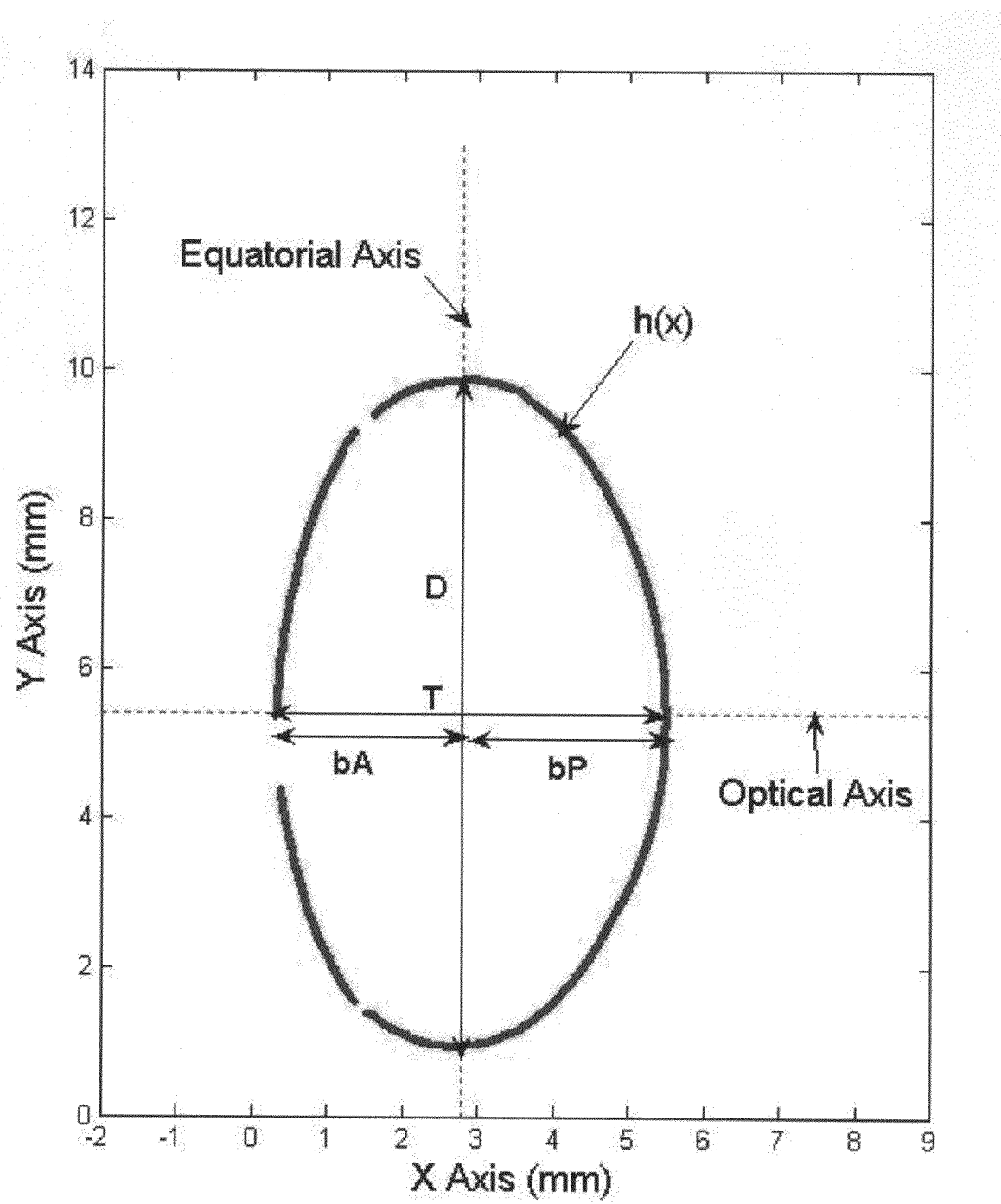
FIG. 3 is a plotted coordinate system showing the One Curve method.

The post-processed images were loaded into Matlab and analyzed in two ways. In the first method, the Two Curves Method (TCM) (FIG. 2), the lens was divided along the equatorial axis to obtain the anterior and posterior surfaces of the lens. In the One Curve Method (OCM) (FIG. 3), the lens was assumed to be symmetric around the optical axis and divided along the optical axis to obtain the contour of half of the lens. The three curves obtained (anterior, posterior and half) were fit to tenth order polynomials using Matlab's curve fitting toolbox. Therefore, as shown in FIG. 2, the coordinate system of the Two Curves method. The equatorial axis is parallel to the X axis and the optical axis is parallel to the Y axis. The data set of pixel coordinates above the equatorial axis corresponds to the posterior segment of the lens, and the set below, corresponds to the anterior segment of the lens. The diameter (D), thickness (T), anterior thickness (bA) and posterior thickness (bP) are shown. p(x) is the posterior TCM polynomial and a(x) is the anterior TCM polynomial. FIG. 3 shows The coordinate system of the One Curve method (OCM). The optical axis is parallel to the X axis and the equatorial axis is parallel to the Y axis. The data set of the pixel coordinates above the optical axis was used in this method. The diameter (D), thickness (T), anterior thickness (bA) and posterior thickness (bP) are shown. h(x) is the OCM polynomial.

In the TCM, the equatorial diameter (D) was estimated as the distance between the points of intersection of the two polynomials representing the anterior and posterior surfaces of the lens. The points of intersection of the two polynomials were determined by matching the two polynomials up to two decimal places. The sagittal thickness (T) was estimated as the distance between the maximum value of the polynomial representing the posterior surface and the minimum value of the polynomial representing the anterior surface. The anterior sagittal thickness (bA) and the posterior sagittal thickness (bP) were also obtained from the fits. The cross-sectional area (CSA) of the lens was computed by integrating the fits delineated by the equatorial axis. Assuming rotational symmetry around the optical axis, the surface area (SA) was estimated by computing the surface of revolution of the fits around the optical axis. The volume (V) of the lens was estimated by computing the solid of revolution of the cross-sectional plane around the optical axis. The equations for the polynomials, cross-sectional area (CSA), surface area (SA) and volume (V) for the TCM are listed in Table 1.

In the OCM, the thickness (T) was estimated as the distance between the points of intersection of the polynomial and its mirror image at the optical axis. Diameter (D) was estimated as the distance between the maximum value of the polynomial and the minimum value of its reflection. The anterior sagittal thickness (bA) and the posterior sagittal thickness (bP) were also obtained from the fits. The cross-sectional area (CSA) of the lens was computed by integrating the curve delineated by the optical axis. Assuming rotational symmetry, surface area (SA) of the lens was estimated by computing the surface of revolution of the fitted curve around the optical axis and the volume (V) of the lens was estimated by computing the solid of revolution of the cross-sectional plane around the optical axis. The equations for the polynomial, cross-sectional area (CSA), surface area (SA) and volume (V) in the OCM are listed in Table 1.

Data Analysis

Figure 4:
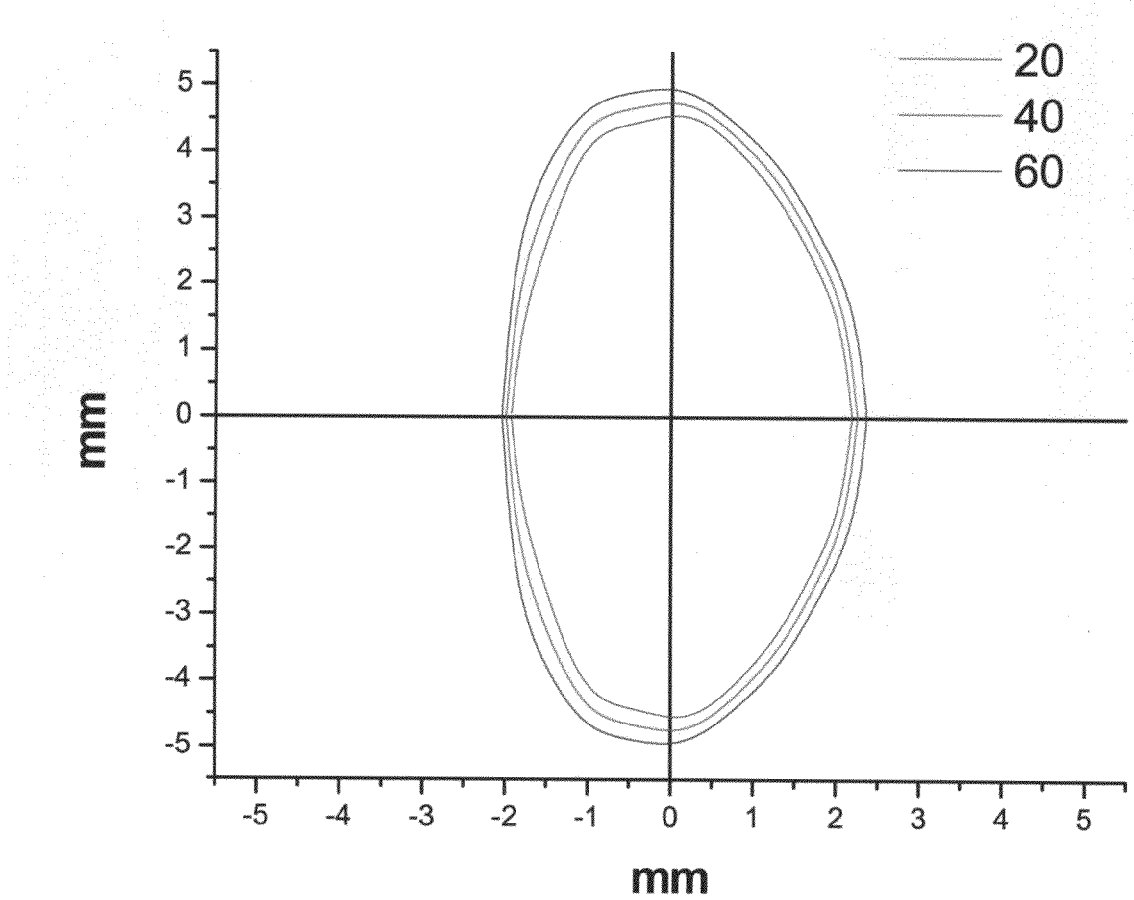
FIG. 4 is a plotted coordinate system showing the One Curve method illustrating three lenses of varying age.
Figure 5:
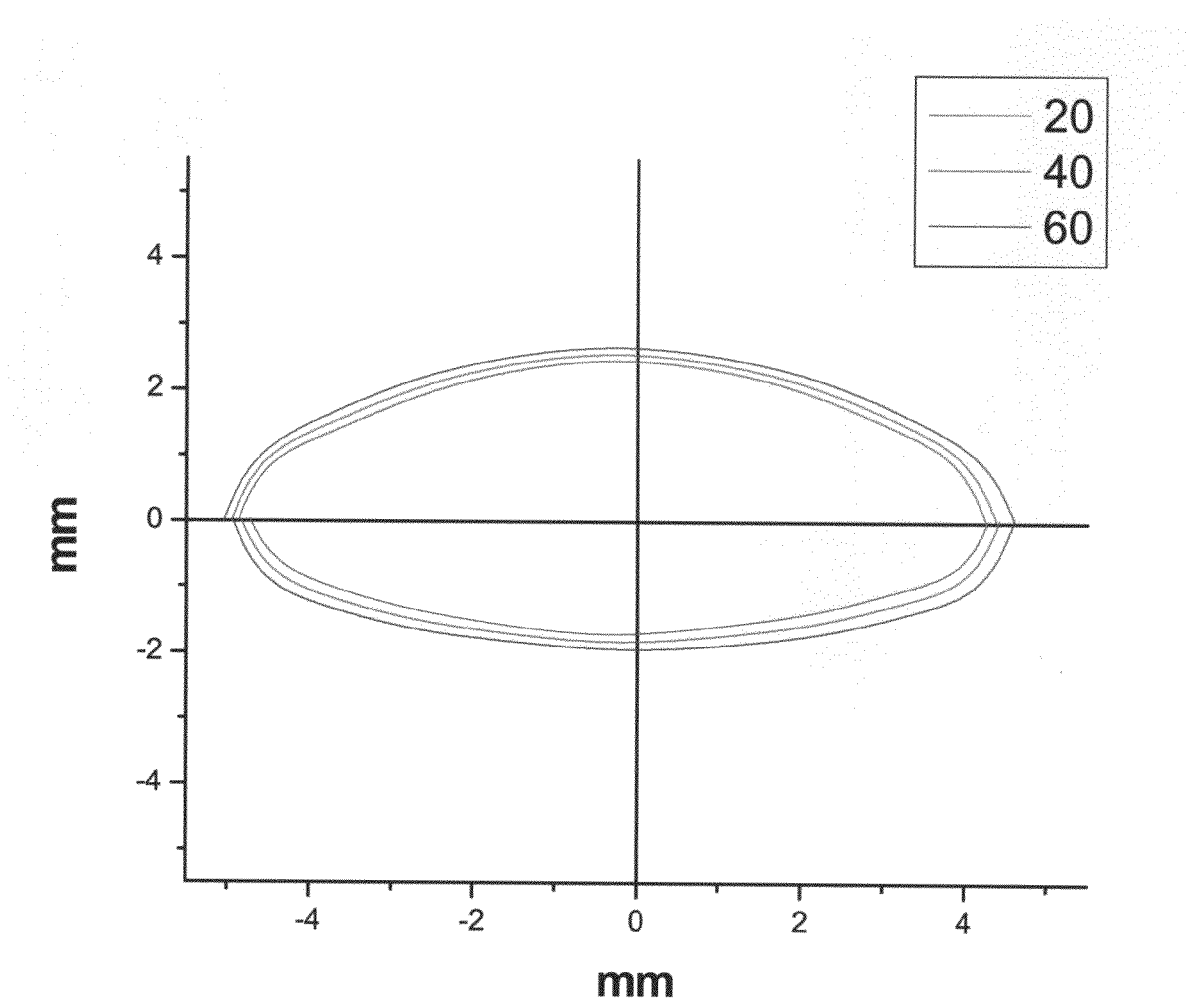
FIG. 5 is a plotted coordinate system showing the Two Curve method illustrating three lenses of varying age.

The coefficients of the tenth order polynomial for each of the three curves were analyzed as a function of age. Using these coefficients, the lens shapes for 20, 40 and 60 year old lenses were plotted. The OCM curve was plotted from x=−bA to x=bP. The resulting curve was translated in the vertical direction by a factor y=−D/2 to center the lens in the coordinate system. The mirror image was obtained by flipping the curve around the X axis (FIG. 4). FIG. 4 shows an OCM model of 20 (green), 40 (red) and 60 (blue) year old lenses. The OCM curve was plotted from −bA to bP and the y parameter was adjusted by a factor of −D/2. The mirror image was obtained by flipping the curve around the X axis. Overshoots were removed by limiting the points to positive y values for the OCM curve and negative y values for its mirror image. Overshoots were removed by limiting the points to positive y values for the OCM curve and negative y values for its mirror image. The TCM model was not symmetrical around the optical axis; therefore the anterior and posterior segments were plotted from x=−D/2−0.25 to x=D/2−0.25. The anterior curve was translated by y=−bA and the posterior curve by y=bP to center the lens in the coordinate system. (FIG. 5). FIG. 5 shows a TCM model of 20 (green), 40 (red) and 60 (blue) year old lenses. The TCM model was not symmetrical around the optical axis; therefore the anterior and posterior surfaces were plotted from −D/2−0.2 to D/2. The y parameter of the anterior surface was adjusted by a factor of −bA and the y parameter of the anterior segment was adjusted by a factor of bP. Overshoots were removed by limiting the points to positive y values for the posterior surface and negative y values for the anterior surface.

Overshoots were removed by limiting the points to positive y values for the posterior surface and negative y values for the anterior surface. For each of the methods the dimensions used (D, bA and bP), were the linear regressions obtained from that method itself. The diameter (D), thickness (T), anterior thickness (bA), posterior thickness (bP), cross-sectional area (CSA), surface area (SA) and volume (V) obtained from the two methods were also analyzed as a function of age.

Results

Figure 8:
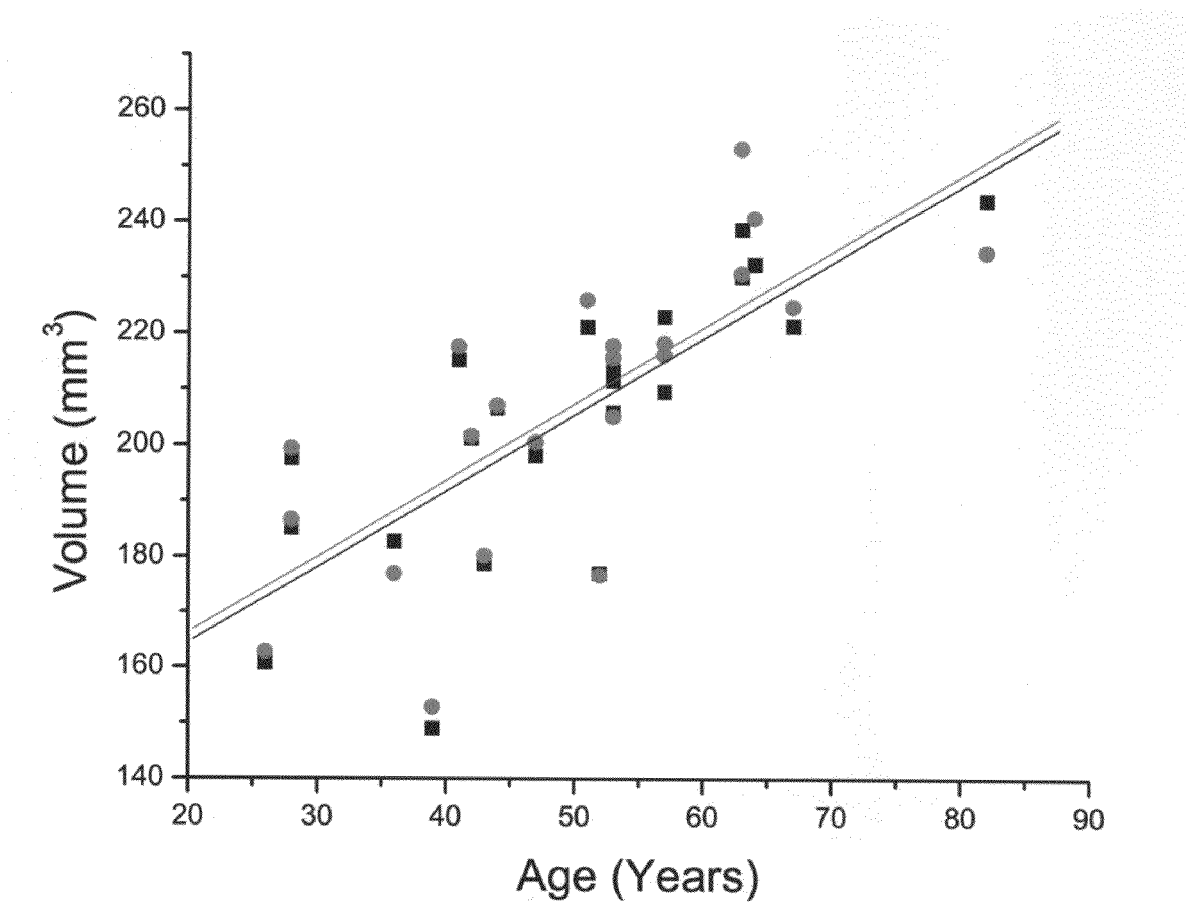
Figure 9:
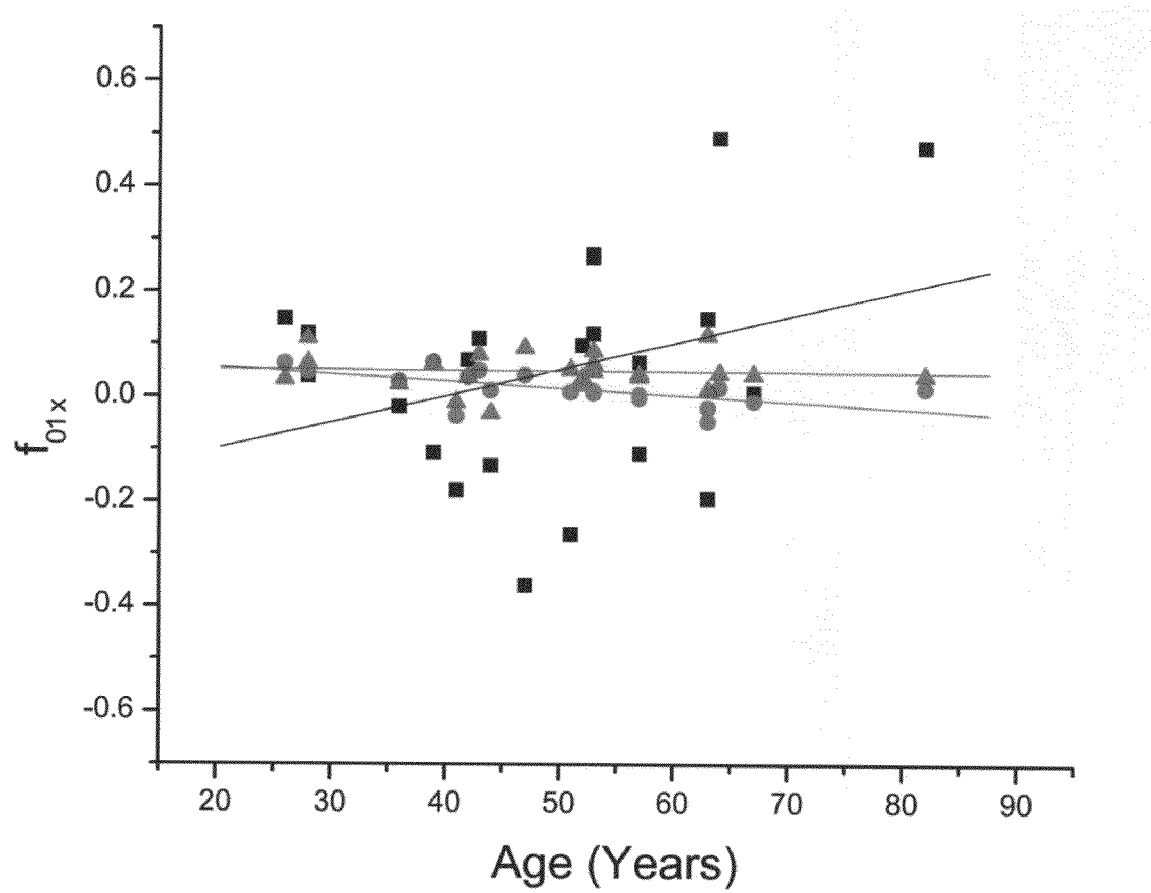
FIG. 9 is a graph showing age-related changes in the first coefficient of One Curve method, the anterior curve of the Two Curve method, and the posterior curve of the Two Curve method.
Figure 10:
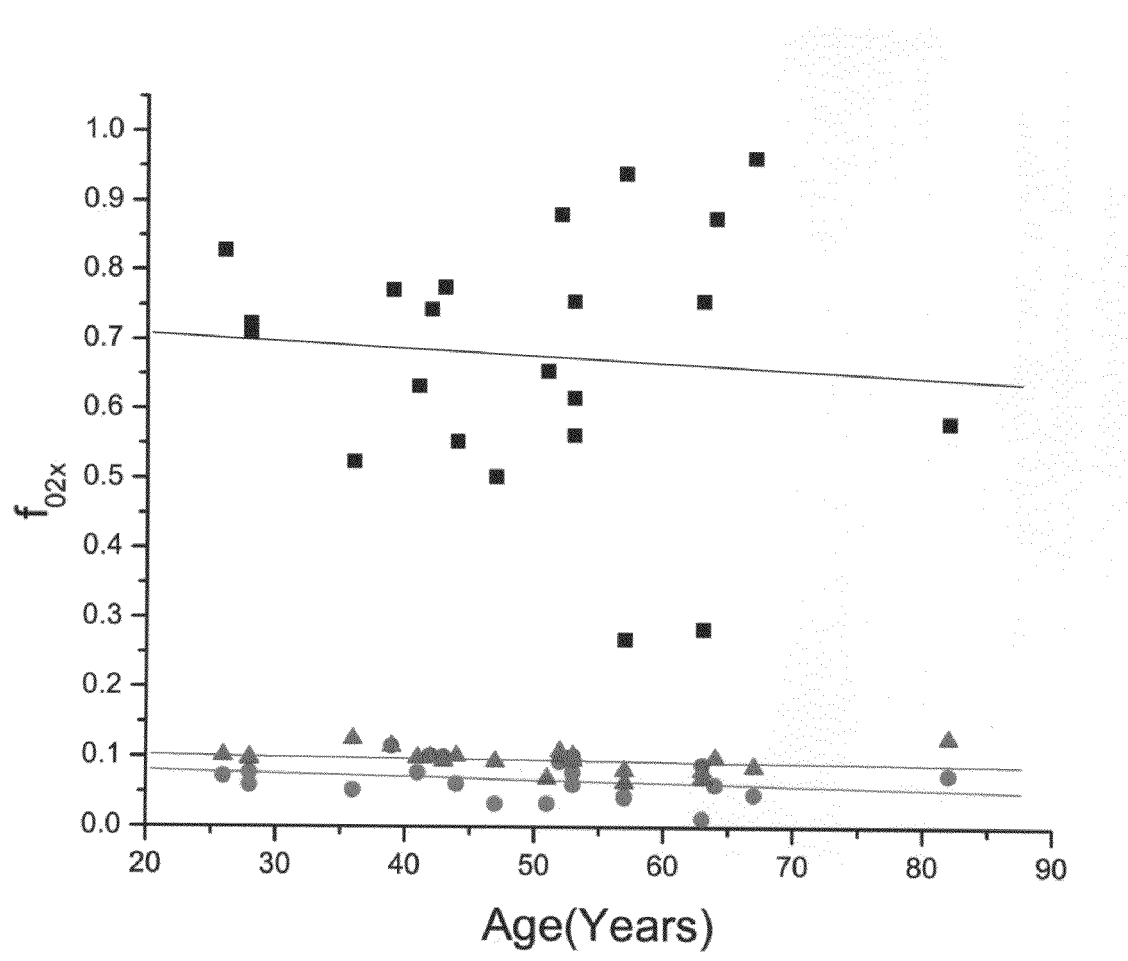
FIG. 10 is a graph showing age-related changes in the second coefficient of One Curve method, the anterior curve of the Two Curve method, and the posterior curve of the Two Curve method.
Figure 11A:
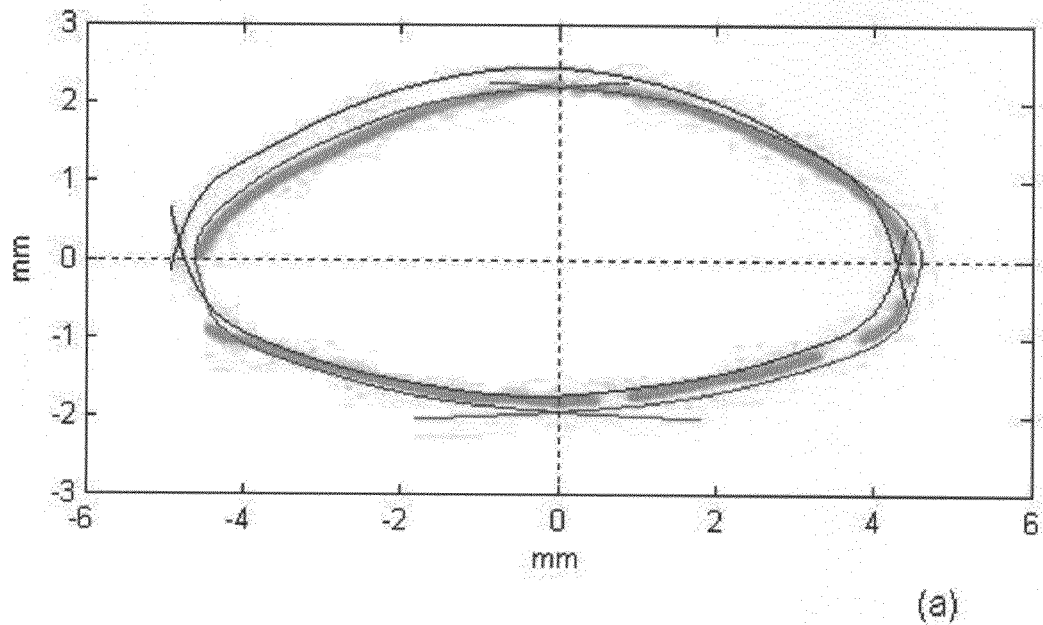
FIGS. 11 a-h are graphs showing TCM and OCM models superimposed on the profile of lenses of varying ages.
Figure 11B:
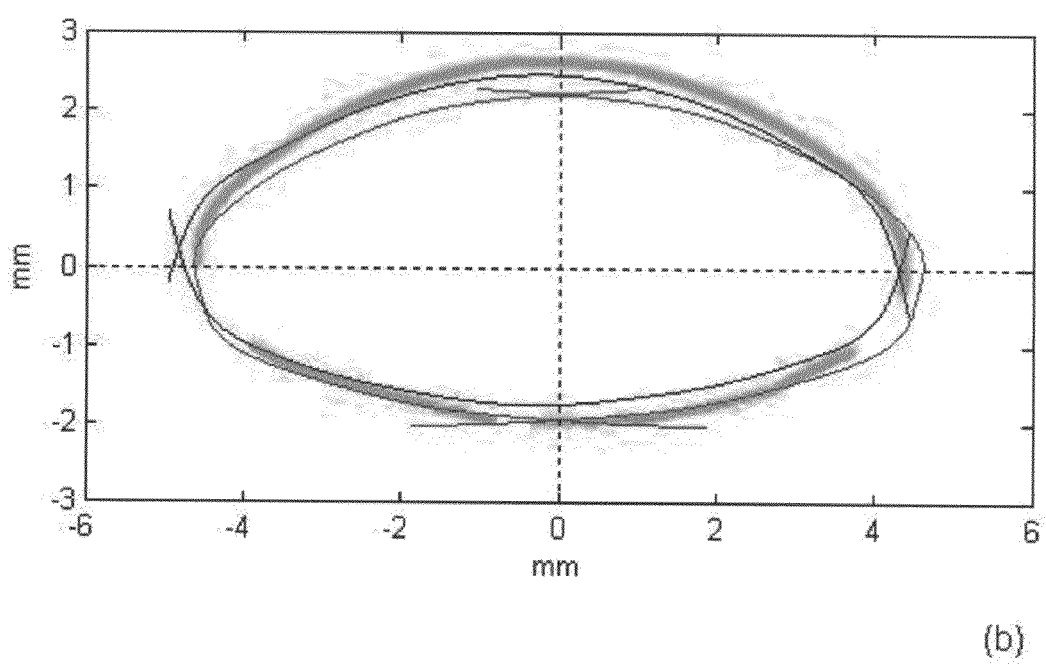
Figure 11C:
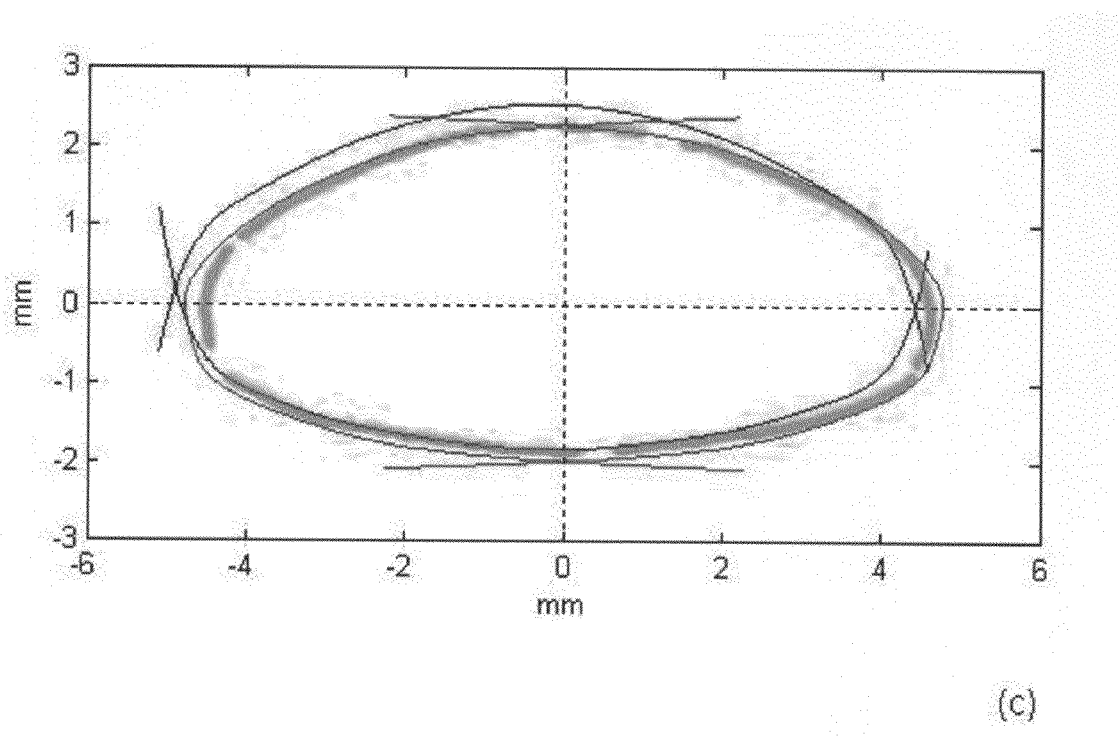
Figure 11D:
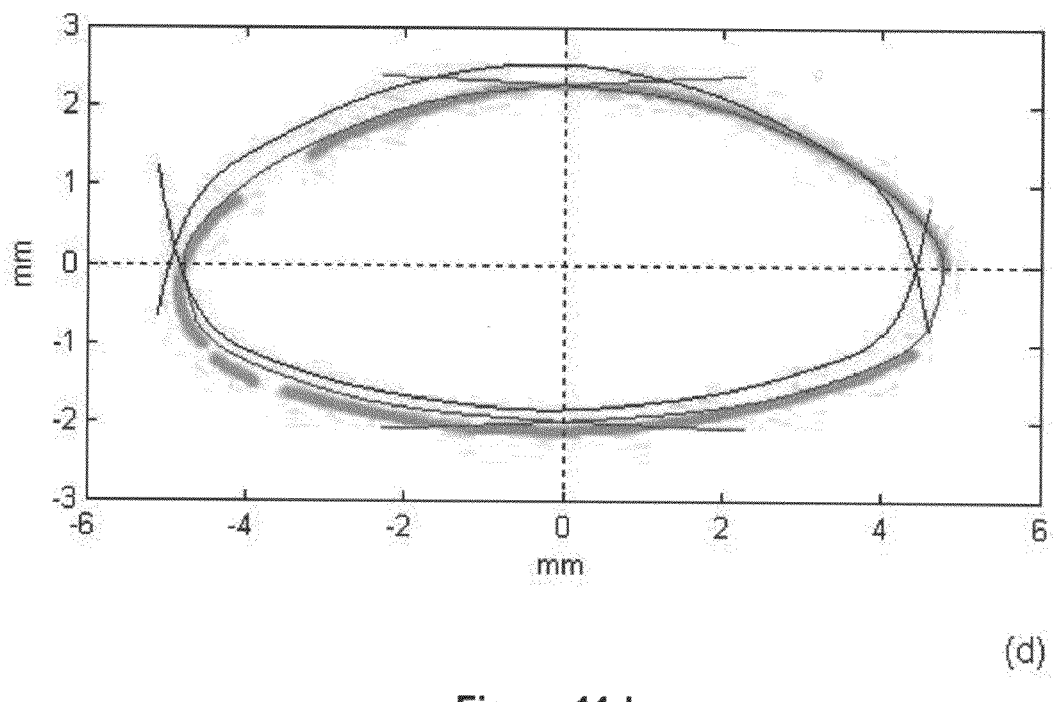
Figure 11E:
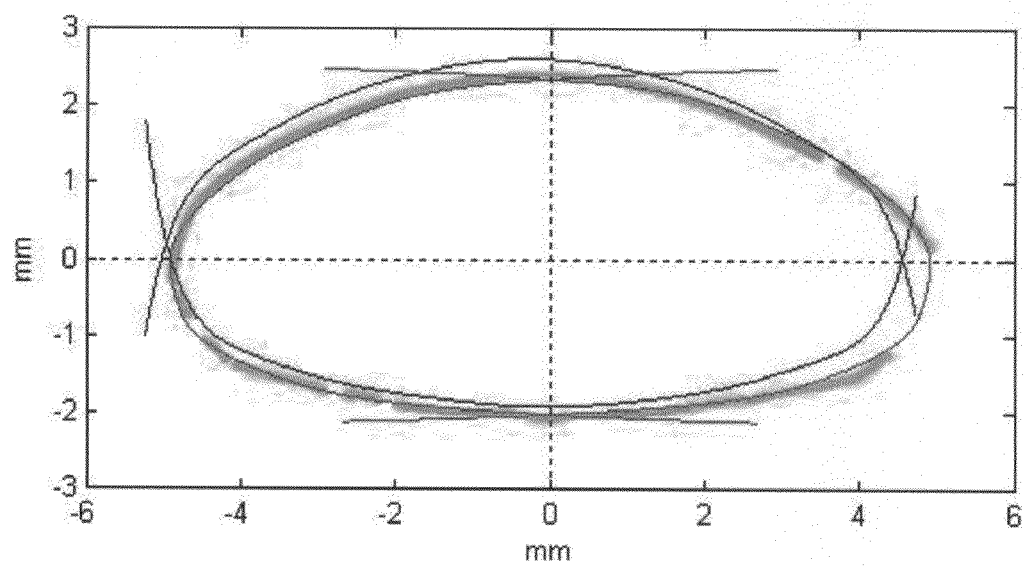
Figure 11F:
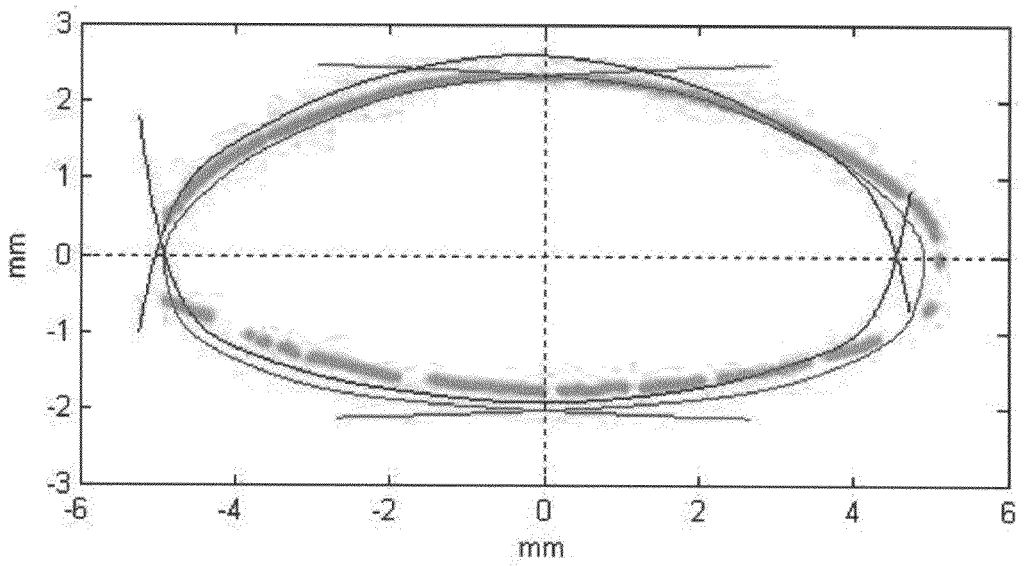
Figure 11G:
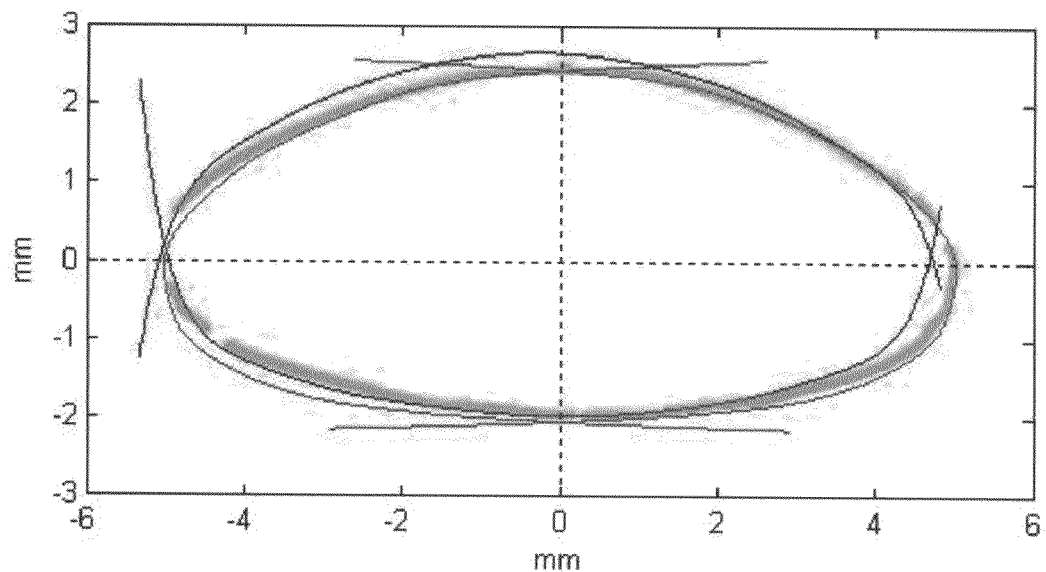
Figure 11H:
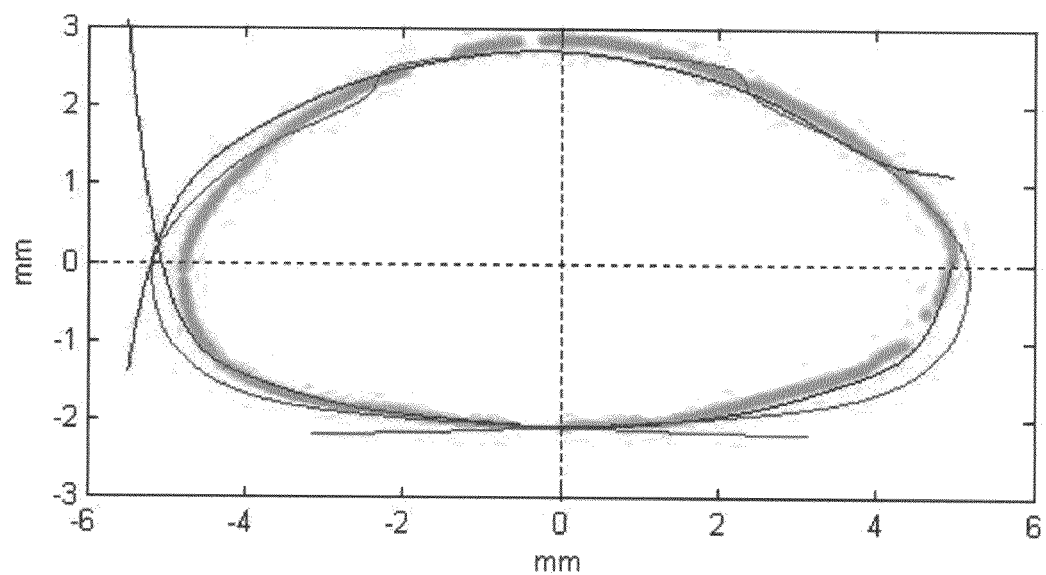

The root mean squared errors for the fits ranged from 41 to 122 um for the OCM, 8 to 30 μm for the posterior surface of the TCM and 11 to 41 μm for the anterior surface of the TCM. The results (Table 2 and FIGS. 6 to 8) show that all dimensions increase with age. The coefficients of the posterior surface of the TCM did not display a significant trend with age (Table 3). Coefficients of the first, fifth and ninth term of the anterior surface decreased with age and coefficients of the third and seventh terms increased with age. The coefficients of even powers of the anterior surface polynomial did not show any significant trend with age. The coefficients of the eighth term of the OCM curve significantly increased with age, the coefficient of all other terms did not change significantly with age. FIGS. 9 and 10 show the age dependency of the first and second coefficients of the three curves. All coefficients displayed a high percentage of uncertainty. The uncertainty of the coefficients that were statistically significant trend with age (p<0.1) ranged from 23% to 57%. Both models were superimposed on lens profiles of various ages (FIGS. 11*a-h*).

Shadow-photographs of isolated ex-vivo lenses were analyzed to obtain age dependent models through linear regression of the coefficients of the polynomial fits. The lenses were analyzed with two methods, the OCM, where half the contour of the lens was modeled assuming symmetry around the optical axis and the TCM, where the contour of the anterior and posterior surfaces was analyzed separately.

The three surfaces from the two methods were fit to tenth order polynomials. This was the lowest order that provided the best fit especially near the equatorial regions. A higher order augmented conic function similar to that which was used by Rosen et al. did not accurately represent the shape of the lens around the equatorial regions. An advantage of using conic functions is that the optical properties of the lens such as the radii of curvature can be easily calculated. Although the radii of curvature can be calculated from the second derivative of the polynomials, there is high variability due to the degree of uncertainty of the coefficients. Polynomials are therefore better suited for modeling the whole lens shape, while conic functions are more suitable for optical modeling of the lens.

Figure 6:
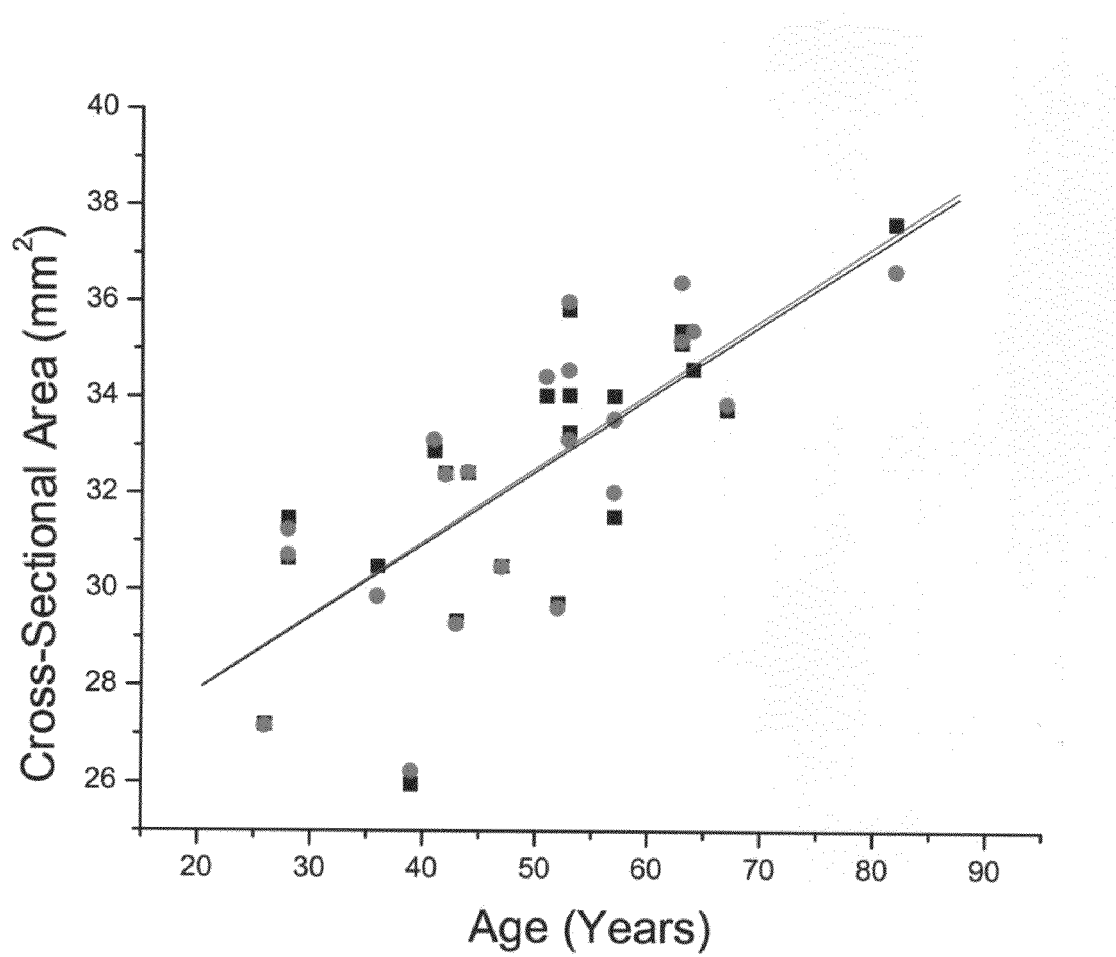
FIGS. 6-8 are graphs showing age-related changes in cross-sectional areas (FIG. 6); surface area (FIG. 7); and volume (FIG. 8) of the human lens for the One Curve and Two Curve methods.
Figure 7:
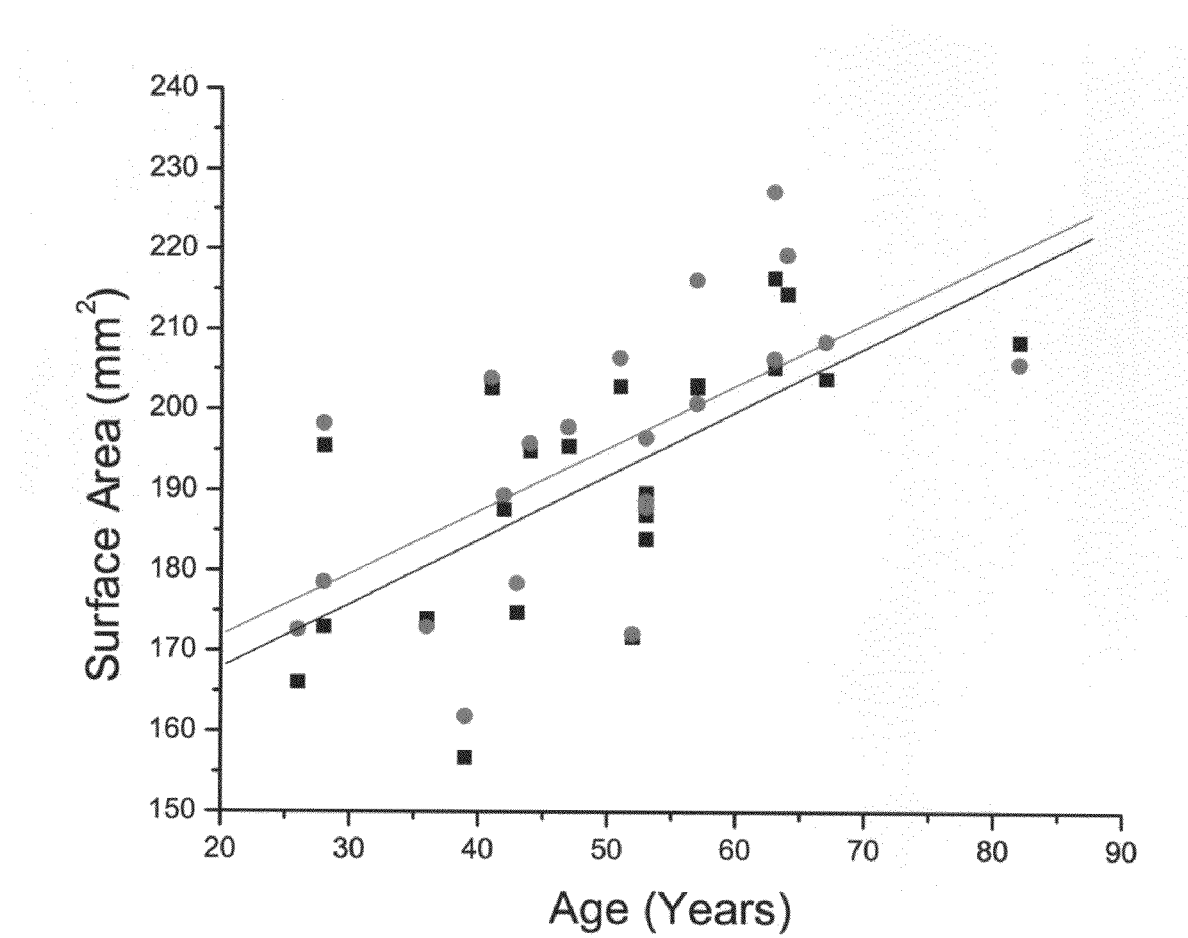

The diameter and thickness of the lens estimated by the two models (FIGS. 3 and 4) are in accordance with measurements reported earlier (Rosen et al. 2006). The anterior and posterior thickness estimated by TCM matches the reported measurements, but those estimated by OCM slightly pushes the equatorial axis towards the posterior surface of the lens. Lens cross-sectional area (CSA) obtained from both methods range from 27 to 37 $mm^2$ (FIG. 6). FIG. 6 shows age related changes in Cross-Sectional Area (CSA) of the human lens for the One Curve Method(OCM; ■) and the Two Curves Method(TCM; ●). Linear fits of the data indicated CSA=24.86 (±1.6)+0.15 (±0.03)*Age ($R^2$=0.56; p<0.0001) for OCM and CSA=24.85 (±1.6)+0.15 (±0.03)*Age ($R^2$=0.55; p<0.0001) for TCM. FIG. 7 shows Age related changes in Surface Area (SA) of the human lens for the One Curve Method (OCM; ■) and the Two Curves Method (TCM; ●). Linear fits of the data indicated SA=151.98 (±9.9)+0.8 (±0.2)*Age ($R^2$=0.46; p=0.0005) for OCM and SA=156.32 (±10.78)+0.78 (±0.21)*Age ($R^2$=0.41; p=0.0014) for TCM.

For the age range of 20 to 55 Strenk et al. (2004) reported a CSA range of 22 to 30 $mm^2$ for the accommodated eye, using MRI images. Examination of data from Glasser and Campbell (1999) for this age range revealed a CSA range of 18 to 23 $mm^2$. The difference in measurements could be due to the lower resolution of the MRI images.

Surface area (SA) of the lens (FIG. 8) increased with age, indicating that there is increased tension on the lens capsule as the lens ages. The range of surface areas obtained from the OCM was 172 to 217 $mm^2$, and from the TCM was 177 to 220 $mm^2$, which is larger than the data reported by Hermans et al (2007). This could be because their model was based on measurements from Scheimpflug images and the equatorial regions were modeled with conic functions. FIG. 8 shows age related changes in Volume (V) of the human lens for the One Curve Method (OCM; ■) and the Two Curves Method (TCM; ●). Linear fits of the data indicated V=137.1 (±12.87)+1.37 (±0.25)*Age ($R^2$=0.6; p<0.0001) for OCM and V=138.85 (±14.1)+1.37 (±0.27)*Age ($R^2$=0.55; p<0.0001) for TCM. FIG. 9 shows age related changes in the first coefficient of the OCM curve ($f_{01h}$; ▮), the anterior curve of the TCM ($f_{01a}$; ●) and the posterior curve of the TCM ($f_{01p}$; ▲). Linear fits of the data indicated $f_{01h}$=−0.19917 (±0.17)+0.00502 (±0.003)*Age ($R^2$=0.11; p=0.1408), $f_{01a}$=0.08105 (±0.02)+−0.00129 (±3.8E−4)*Age ($R^2$=0.36; p=0.003) and $f_{01p}$=0.05184 (±0.03)+−8.2014E−5 (±5.6E−4)*Age ($R^2$=0.001; 0.8858). FIG. 10 shows age related changes in the second coefficient of the OCM curve ($f_{02h}$; ■), the anterior curve of the TCM ($f_{02a}$; ●) and the posterior curve of the TCM ($f_{02p}$; ▲). Linear fits of the data indicated $f_{02h}$=0.72942 (±0.15)+−0.00103 (±0.003)*Age ($R^2$=0.006; p=0.7302), $f_{02a}$=0.08912 (±0.02)+−4.35778E−4 (±4.1E−4)*Age ($R^2$=0.05; p=0.3031) and $f_{02p}$=0.10586 (±0.01)+−2.07467E−4 (±2.5E−4)*Age ($R^2$=0.03; p=0.4221).

The main goal of the present study was to develop an analytical model of the human crystalline lens that can be used in FE modeling. This was accomplished by using the linear regression of the coefficients of the polynomial fits. To verify that the equations can be used, shapes of 20, 40 and 60 years old lenses were plotted. The TCM model (FIG. 5) shows that the anterior and posterior surfaces of the lens do not meet at the equatorial axis on one side of the lens. This could be due to the high variability of the age dependent terms in the coefficients of the posterior surface polynomial. Another reason for this could be that some of the lenses look tilted in the images. Twelve (12) lenses appeared tilted with an angle of less than ten degrees. The TCM model is also longer on one side of the optical axis. Both these features are not observed in the OCM model (FIG. 4) because this model uses only one half of the lens and assumes symmetry around the optical axis. TCM and OCM models superimposed on lens profiles of various ages (FIG. 11) show that the OCM model provides a closer estimate of the lens shape than the TCM model. For both models, the lens shape is reliably modeled only until age 70. Beyond that the shape is inconsistent with the shape of the lens. This could be due to the high variability in the higher order coefficients of the polynomials. FIG. 11 shows TCM (blue) and OCM (red) models superimposed on the profile of lenses (cyan) of age (a) 26 (b) 28 (c) 43 (d) 44 (e) 57 (f) 57 (g) 67 (h) 82.

According to embodiments of the present invention, the methods described herein can both be used to obtain dimensions of the human crystalline lens. However, to obtain the lens shape the OCM method is preferred. Even though the OCM fits have a higher root mean square error than the TCM fits, the single curve design of the OCM model ensures that there are no discontinuities on the surface of the lens at the equatorial axis.

Of the two age dependant models of the isolated ex-vivo human crystalline lens described herein, the OCM model provides a closer estimate of the shape of the lens. Furthermore, the OCM model describes the lens with only one mathematical equation making it a simpler model. This model can serve to improve FE-models of lenses.

TABLES

TABLE 1

Equations of polynomials, cross-sectional area (CSA), surface area (SA) and volume (V) for the Two Curves Method (TCM) and the One Curve Method (OCM). p(x) is the posterior polynomial, a(x) is the anterior polynomial and h(x) is the polynomial representing half the contour of the lens. $f_{01p}$ to $f_{10p}$, $f_{01a}$ to $f_{10a}$ and $f_{01h}$ to $f_{10h}$ are the coefficients of the three polynomials.

Two Curves Method (TCM)

$$p(x) = y_0 - f_{01p}(x - x_0) - f_{02p}(x - x_0)^2 - f_{03p}(x - x_0)^3 - f_{04p}(x - x_0)^4 - f_{05p}(x - x_0)^5 - f_{06p}(x - x_0)^6 - f_{07p}(x - x_0)^7 - f_{08p}(x - x_0)^8 - f_{09p}(x - x_0)^9 - f_{10p}(x - x_0)^{10}$$

$$a(x) = y_0 - f_{01a}(x - x_0) - f_{02a}(x - x_0)^2 + f_{03a}(x - x_0)^3 - f_{04a}(x - x_0)^4 + f_{05a}(x - x_0)^5 - f_{06a}(x - x_0)^6 + f_{07a}(x - x_0)^7 - f_{08a}(x - x_0)^8 + f_{09a}(x - x_0)^9 - f_{10a}(x - x_0)^{10} +$$

$$CSA = \int_{x_1}^{x_2} [p(x) - a(x)] \, dx$$

$$SA = \int_{x_1}^{x_2} \pi |x_{op} - x| \sqrt{1 + (p'(x))^2} \, dx + \int_{x_1}^{x_2} \pi |x_{op} - x| \sqrt{1 + (a'(x))^2} \, dx$$

$$V = \int_{x_1}^{x_2} \pi |x_{op} - x| (p(x) - a(x)) \, dx$$

One Curve Method (OCM)

$$h(x) = y_0 - f_{01h}(x - x_0) - f_{02h}(x - x_0)^2 - f_{03h}(x - x_0)^3 - f_{04h}(x - x_0)^4 - f_{05h}(x - x_0)^5 - f_{06h}(x - x_0)^6 - f_{07h}(x - x_0)^7 - f_{08h}(x - x_0)^8 -$$

TABLE 1-continued

Equations of polynomials, cross-sectional area (CSA), surface area (SA) and volume (V) for the Two Curves Method (TCM) and the One Curve Method (OCM). p(x) is the posterior polynomial, a(x) is the anterior polynomial and h(x) is the polynomial representing half the contour of the lens. $f_{01p}$ to $f_{10p}$, $f_{01a}$ to $f_{10a}$ and $f_{01h}$ to $f_{10h}$ are the coefficients of the three polynomials.

$$f_{09h}(x - x_0)^9 - f_{10h}(x - x_0)^{10} -$$

$$CSA = 2\left(\left(\int_{x_1}^{x_2} h(x) \, dx\right) - (x_2 - x_1) y_{op}\right)$$

$$SA = \int_{x_1}^{x_2} 2\pi |h(x) - y_{op}| \sqrt{1 + (h'(x))^2} \, dx$$

$$V = \int_{x_1}^{x_2} \pi (y_{op} - h(x))^2 \, dx$$

Table 2: Dimensions of the crystalline lens obtained from the One Curve Method (OCM) and the Two Curves methods (TCM) (n=22) compared to dimensions measured from images manually in Rosen et al.

TABLE 2

Table 2: Dimensions of the crystalline lens obtained from the One Curve Method (OCM) and the Two Curves methods (TCM) (n = 22) compared to dimensions measured from images manually in Rosen et al.

| Dimension | One Curve Method | Two Curves Method | Rosen et al |
|---|---|---|---|
| Diameter (D) [mm] | 8.68 (±0.33) + 0.02 (±0.01) * Age ($R^2 = 0.28$; p = 0.0103) | 8.83 (±0.36) + 0.02 (±0.007) * Age ($R^2 = 0.23$; p = 0.0245) | 8.7 (±0.14) + 0.0138 (±0.002) * Age ($R^2 = 0.57$; p < 0.0001) |
| Thickness (T) [mm] | 3.92 (±0.21) + 0.01 (±0.004) * Age ($R^2 = 0.26$; p = 0.015) | 3.91 (±0.21) + 0.011 (±0.004) * Age ($R^2 = 0.25$; p = 0.0171) | 3.97 (±0.16) + 0.0123 (±0.003) * Age ($R^2 = 0.48$; p < 0.0001) |
| Anterior Thickness (bA) [mm] | 1.96 (±0.12) + 0.003 (±0.002) * Age ($R^2 = 0.08$; p = 0.1846) | 1.59 (±0.18) + 0.006 (±0.003) * Age ($R^2 = 1$; p < 0.0001) | 1.65 (±0.075) + 0.0049 (±0.001) * Age ($R^2 = 0.45$; p < 0.0001) |
| Posterior Thickness (bP) [mm] | 2.08 (±0.17) + 0.007 (±0.003) * Age ($R^2 = 0.16$; p = 0.0608) | 2.32 (±0.14) + 0.005 (±0.003) * Age ($R^2 = 0.13$; p = 0.1053) | 2.33 (±0.11) + 0.0074 (±0.002) * Age ($R^2 = 0.44$; p < 0.0001) |

TABLE 3

Coefficients of $10^{th}$-order polynomials representing half curve ($f_{xxh}$), anterior ($f_{xxa}$) and posterior segment ($f_{xxp}$) of the lens, where $f_{xxx} = A + B \times Age$ (n = 22). Asterisk (*) denotes coefficients with a significant trend with age (p < 0.1).

| Coefficient | A | % variability of A | B | % variability of B | $R^2$ | p value |
|---|---|---|---|---|---|---|
| One Curve Method | | | | | | |
| $f_{01h}$ | −0.19917 ± 0.1681 | 84 | 0.00502 ± 0.00327 | 65 | 0.11 | 0.1408 |
| $f_{02h}$ | 0.72942 ± 0.15146 | 21 | −0.00103 ± 0.00295 | 286 | 0.006 | 0.7302 |
| $f_{03h}$ | 1.00775 ± 0.41008 | 41 | −0.00958 ± 0.00799 | 83 | 0.07 | 0.2444 |
| $f_{04h}$ | −0.42279 ± 0.24758 | 59 | 0.00134 ± 0.00482 | 359 | 0.004 | 0.7832 |
| $f_{05h}$ | −0.99849 ± 0.43377 | 43 | 0.00926 ± 0.00845 | 91 | 0.06 | 0.2863 |
| $f_{06h}$ | 0.55247 ± 0.14001 | 25 | −0.00432 ± 0.00273 | 63 | 0.11 | 0.1291 |
| $f_{07h}$ | 0.33737 ± 0.16734 | 50 | −0.00294 ± 0.00326 | 111 | 0.04 | 0.3774 |
| $f_{08h}$* | −0.20449 ± 0.04665 | 23 | 0.00184 ± 9.08703E-4 | 49 | 0.17 | 0.0564 |
| $f_{09h}$ | −0.04011 ± 0.02273 | 57 | 3.15643E-4 ± 4.42733E-4 | 140 | 0.02 | 0.4841 |
| $f_{10h}$ | 0.02513 ± 0.00708 | 28 | −2.30395E-4 ± 1.37994E-4 | 60 | 0.12 | 0.1106 |

TABLE 3-continued

Coefficients of $10^{th}$-order polynomials representing half curve ($f_{xxh}$), anterior ($f_{xxa}$) and posterior segment ($f_{xxp}$) of the lens, where $f_{xxx} = A + B \times Age$ (n = 22). Asterisk (*) denotes coefficients with a significant trend with age (p < 0.1).

| Coefficient | A | % variability of A | B | % variability of B | $R^2$ | p value |
|---|---|---|---|---|---|---|
| Two Curve Method - Anterior Surface | | | | | | |
| $f_{01a}$* | 0.08105 ± 0.01967 | 24 | −0.00129 ± 3.83163E−4 | 30 | 0.36 | 0.003 |
| $f_{02a}$ | 0.08912 ± 0.02117 | 24 | 4.35778E−4 ± 4.12304E−4 | 95 | 0.05 | 0.3031 |
| $f_{03a}$* | −0.02801 ± 0.00777 | 28 | 4.13181E−4 ± 1.5138E−4 | 37 | 0.27 | 0.0129 |
| $f_{04a}$ | −0.01087 ± 0.00656 | 60 | 4.24651E−5 ± 1.27745E−4 | 301 | 0.005 | 0.743 |
| $f_{05a}$* | 0.00549 ± 0.00182 | 33 | −7.06647E−5 ± 3.53858E−5 | 51 | 0.17 | 0.0596 |
| $f_{06a}$ | 0.00178 ± 9.769E−4 | 55 | −7.91836E−6 ± 1.90298E−5 | 240 | 0.008 | 0.6818 |
| $f_{07a}$* | −4.49499E−4 ± 1.55388E−4 | 35 | 5.45145E−6 ± 3.02692E−6 | 56 | 0.14 | 0.0868 |
| $f_{08a}$ | −1.34645E−4 ± 6.59708E−5 | 49 | 8.22675E−7 ± 1.2851E−6 | 156 | 0.02 | 0.5293 |
| $f_{09a}$* | 1.29715E−5 ± 4.50894E−6 | 35 | −1.53698E−7 ± 8.7833E−8 | 57 | 0.13 | 0.0954 |
| $f_{10a}$ | 3.77094E−6 ± 1.65749E−6 | 44 | −2.86146E−8 ± 3.22875E−8 | 113 | 0.04 | 0.386 |
| Two Curves Method - Posterior Surface | | | | | | |
| $f_{01p}$ | 0.05184 ± 0.02894 | 56 | −8.2014E−5 ± 5.63696E−4 | 687 | 0.001 | 0.8858 |
| $f_{02p}$ | 0.10586 ± 0.01299 | 12 | −2.07467E−4 ± 2.53136E−4 | 122 | 0.03 | 0.4221 |
| $f_{03p}$ | −0.01144 ± 0.00762 | 67 | 6.97231E−5 ± 1.48425E−4 | 213 | 0.01 | 0.6436 |
| $f_{04p}$ | −0.00626 ± 0.0034 | 54 | −9.64448E−7 ± 6.61874E−5 | 6862 | 0.00001 | 0.9885 |
| $f_{05p}$ | 0.00324 ± 0.00171 | 53 | −2.7504E−5 ± 3.32365E−5 | 120 | 0.03 | 0.4177 |
| $f_{06p}$ | 0.00133 ± 5.51855E−4 | 41 | −4.86461E−6 ± 1.075E−5 | 220 | 0.01 | 0.6558 |
| $f_{07p}$ | −3.39872E−4 ± 1.48794E−4 | 44 | 3.51493E−6 ± 2.89846E−6 | 82 | 0.07 | 0.2394 |
| $f_{08p}$ | −1.18847E−4 ± 3.86712E−5 | 33 | 8.28178E−7 ± 7.53305E−7 | 91 | 0.06 | 0.2847 |
| $f_{09p}$ | 1.17536E−5 ± 4.53044E−6 | 39 | −1.36141E−7 ± 8.82519E−8 | 65 | 0.11 | 0.1386 |
| $f_{10p}$ | 3.63863E−6 ± 1.02971E−6 | 28 | −3.3147E−8 ± 2.00585E−8 | 61 | 0.12 | 0.114 |

For utility, the above algorithm and method may be implemented in a device consisting of a number of modules. Three functional modules are deemed essential. These modules are responsible for the inputting of data (input module) into the algorithm, a module which implements the algorithm of the present invention (processing module), and a module for outputting the calculated description of the lens or prosthetic (output module).

The input module may comprise algorithms and hardware or software facilities for acquiring lens profile data from a data source. For example, via manual data-entry, electronic data transfer or data exchange from another device such as a computer. Other possibilities include object linking and embedding (OLE) methods and open database connectivity (ODBC) common to many computer data exchange protocols. The input module may also be integral to a device for direct biometric measurement of crystalline lens such as optical coherence tomography (OCT), ultrasonography and profilometry.

The processing module will house the computation engine (hardware or software facilities) necessary for carrying out the algorithms and for implementing the method of this invention.

The output module provides the results of the processing module in a format useful to the end-user (whether individual or device). It will consist of hardware and software for outputting mathematical lens profile description in a format compatible with the receiver of the data. This may include hardcopy printouts, electronic data transfer or exchange to another device, object linking and embedding (OLE), open database connectivity (ODBC). Other possibilities include the direct connection from the output module to a device for direct output of crystalline lens or prosthetic shape, such as computer assisted design and manufacturing (CAD or CAM) devices such as lathes, mills, cameras and plotters. The output module (or entire device) may, in sophisticated implementations, be integral to such design and manufacturing machineries.

The invention may be embodied in other specific forms without departing from the spirit or essential characteristics thereof. The present embodiments are therefore to be construed in all respects as illustrative and not restrictive, the scope of the invention being indicated by the claims set forth below rather than by the foregoing description.

All modifications which come within the meaning and range of equivalency of the claims are therefore intended to be embraced therein.

The invention claimed is:

1. A method for describing a shape of a lens, the method comprising at a computational device:
   receiving lens profile data of a lens,
   fitting to the lens profile data a mathematical function comprising mathematically linear combinations of polynomials, wherein a surface profile of one half of the lens, divided along an optical axis, is described by said mathematical function,
   outputting a mathematical lens profile description based on the fitting of said mathematical function,
   wherein outputting a mathematical lens profile description comprises outputting a description of said surface profile of one half of the lens and another half of the lens, symmetric about the optical axis to said surface profile of one half of the lens, said surface profiles intersecting at the optical axis,
   further comprises computing and outputting at least one of a surface area and a volume of a lens described by the intersecting surface profiles.

2. A device for facilitating a description of a lens having an optical axis and an equatorial plane substantially perpendicular to the optical axis, said device comprising:
   hardware providing:
   an input module;
   a processing module; and
   an output module;
   wherein said input module comprises algorithms for acquiring lens profile data of the lens from a data source, and said processing module comprises algorithms for computing a mathematical lens profile description, and said output module comprises algorithms for outputting the mathematical lens profile description to a lens profile description receptacle wherein the algorithms for computing a mathematical lens profile description comprise algorithms for:

fitting to lens profile data acquired by input module, a mathematical function comprising mathematically linear combinations of polynomials, wherein a surface profile of one half of the lens divided along the optical axis of the lens is described by said mathematical function; and wherein the algorithms for a computing mathematical lens profile description further comprises algorithms for computing a description of another half of the lens, symmetric about the optical axis to said surface profile of one half of the lens and wherein the algorithms for computing a mathematical lens profile description further comprises algorithms for generating a description of a surface profile of another half of the lens, said surface profiles intersecting at the optical axis; and further comprises algorithms for computing at least one of a surface area and a volume of a lens described by the intersecting surface profiles.

* * * * *